United States Patent [19]

Campbell et al.

[11] Patent Number: 4,711,882
[45] Date of Patent: Dec. 8, 1987

[54] OCTAHYDRO-6-AZAINDOLE COMPOUNDS, COMPOSITIONS AND USE

[75] Inventors: Simon F. Campbell, Deal; Ryszard J. Kobylecki, Sandwich, both of England

[73] Assignee: Pfizer Inc., New York, N.Y.

[21] Appl. No.: 811,253

[22] Filed: Dec. 19, 1985

[30] Foreign Application Priority Data

Dec. 21, 1984 [GB] United Kingdom ............... 8432532
Jun. 10, 1985 [GB] United Kingdom ............... 8514634

[51] Int. Cl.[4] ............... A61K 31/435; A61K 31/535; C07D 471/04
[52] U.S. Cl. ............... 514/228; 514/229; 514/230; 514/231; 514/232; 514/233; 514/236; 514/253; 514/300; 544/80; 544/127; 544/357; 544/362; 546/113
[58] Field of Search ............... 544/80, 127, 357, 362; 546/113; 514/228, 229, 230, 231, 232, 233, 236, 253, 300

[56] References Cited

PUBLICATIONS

Published Australian Patent Application No. AU-A-23645/84.

Primary Examiner—Robert W. Ramsuer
Attorney, Agent, or Firm—Peter C. Richardson; Lawrence C. Akers; J. Trevor Lumb

[57] ABSTRACT

A series of novel octahydro-6-azaindole dipeptide derivatives have been prepared, including their pharmaceutically acceptable salts and bioprecursors therefor. These particular compounds are inhibitors of the angiotensin converting enzyme and are therefore useful in therapy for the treatment of certain cardiovascular disorders, including heart failure and hypertension. Preferred member compounds include 1-[N-(1-S-ethoxycarbonyl-3-phenylpropyl)-S-alanyl]-2-S-carboxy-6-(N-methylcarbamoyl)-octahydro-6-azaindole, 1-[N-(1-S-ethoxycarbonyl-3-phenylpropyl-S-alanyl]-2-S-carboxy-6-methanesulphonyl-octahydro-6-azaindole and 1-[N-(1-carboxy-3-phenylpropyl)-S-lysyl]-2-carboxy-6-methanesulphonyl-octahydro-6-azaindole, respectively. Methods for preparing these compounds from known starting materials are provided.

20 Claims, No Drawings

OCTAHYDRO-6-AZAINDOLE COMPOUNDS, COMPOSITIONS AND USE

BACKGROUND OF THE INVENTION

This invention relates to certain octahydro-6-azaindole dipeptide derivatives and pharmaceutical compositions thereof which have inhibitory activity against angiotensin converting enzyme and are therefore useful in the treatment of certain cardiovascular disorders including hypertension and heart failure.

The enzyme renin is produced in the kidney, it acts upon an alpha-2-globulin to release a decapeptide angiotensin I. Angiotensin converting enzyme cleaves a terminal dipeptide unit from angiotensin I to produce an octapeptide, angiotensin II, which is a highly potent pressor substance. In addition to a direct pressor effect, angiotensin II stimulates the release of aldosterone which also tends to elevate blood pressure by causing retention of sodium chloride and water. Abnormal activation of the renin-angiotensin hormonal control system is thought to be an important contributory factor in certain types of hypertensive disease and cogestive heart failure and inhibition of angiotensin converting enzyme is now well established as an effective approach in the treatment of these conditions.

SUMMARY OF THE INVENTION

According to the present invention, there are provided compounds having inhibitory activity against angiotensin converting enzyme of the formula:

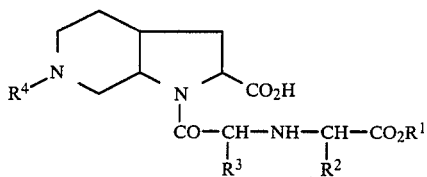

(I)

and pharmaceutically acceptable salts thereof and bioprecursors therefor, wherein:

$R^1$ is H, $C_1$–$C_6$ alkyl, $C_2$–$C_6$ alkenyl or aryl-($C_1$–$C_4$ alkyl);

$R^2$ is $C_1$–$C_6$ alkyl, $C_2$–$C_6$ alkenyl, $C_3$–$C_7$ cycloalkyl or substituted $C_1$–$C_6$ alkyl in which the substituent is halo, hydroxy, $C_1$–$C_6$ alkoxy, aryl, aryloxy, aryl-($C_1$–$C_4$ alkoxy), $C_3$–$C_7$ cycloalkyl, —$NR^5R^6$, —$NHCOR^5$, —$NHCO_2R^7$, guanidino, $C_1$–$C_4$ alkylthio, arylthio, aryl-($C_1$–$C_4$ alkyl)thio or a heterocyclyl group;

$R^3$ is $C_1$–$C_6$ alkyl, $C_3$–$C_7$ cycloalkyl or a substituted $C_1$–$C_6$ alkyl group in which the substituent is —$NHCOR^5$, —$NHCO_2R^7$, —$NR^5R^6$, hydroxy, halo, —$CONR^5R^6$, $C_3$–$C_7$ cycloalkyl, guanidino, —$CO_2H$, —$CO_2(C_1$–$C_4$ alkyl), $C_1$–$C_4$ alkoxy, $C_1$–$C_4$ alkylthio, aryl or a heterocyclyl group;

$R^4$ is —$COR^5$, —$CO_2R^7$, —$SO_2R^7$, —$SO_2NR^5R^6$, —$CONR^5R^6$, —$CON(R^5)SO_2R^7$ or —$CON(R^5)COR^7$, wherein $R^5$ and $R^6$ are each independently H, $C_1$–$C_6$ alkyl, $C_3$–$C_7$ cycloalkyl, aryl, heterocyclyl or a substituted $C_1$–$C_6$ alkyl group in which the group is substituted by one or more halo atoms or a hydroxy, $C_3$–$C_7$ cycloalkyl, aryl, heterocyclyl or —$NR^8R^9$ group wherein $R^8$ and $R^9$ are each independent H, $C_1$–$C_4$ alkyl, —$CO(C_1$–$C_4$ alkyl) or aryl; or the two groups $R^5$ and $R^6$ when attached to nitrogen may be taken together with the nitrogen atom to form a pyrrolidinyl, piperidino, morpholino, piperazinyl or N-($C_1$–$C_4$ alkyl)-piperazinyl group;

and $R^7$ is as defined for $R^5$ but not including hydrogen.

In the above definition, unless otherwise indicated, alkyl groups having three or more carbon atoms may be straight or branched-chain. The term aryl as used herein means an aromatic hydrocarbon group such as phenyl and naphthyl which may optionally be substituted with, for example OH, CN, $CF_3$, $C_1$–$C_4$ alkyl, $C_1$–$C_4$ alkoxy, halo, amino or mono or di($C_1$–$C_4$ alkyl)amino groups. Halo means fluoro, chloro, bromo or iodo. The term heterocyclyl group means a 5 or 6 membered nitrogen, oxygen or sulphur containing heterocyclic group which may be saturated or unsaturated and which may optionally include a further one or two nitrogen atoms in the ring and which may optionally be benzofused or substituted with for example, halo, $C_1$–$C_4$ alkyl, hydroxy, carbamoyl, oxo, $NH_2$ or mono or di-($C_1$–$C_4$ alkyl)amino groups. Particular examples include pyridyl, thienyl, furyl, indolyl, benzthienyl, imidazolyl, thiazolyl, pyrrolidinyl, piperidino, morpholino and piperazinyl groups.

The bicyclic system referred to herein as octahydro-6-azaindole may alternatively be named systematically as octahydro-1H-pyrrolo[2,3-c]pyridine. The hydrogen atoms attached to the ring junction carbon atoms are preferably in the cis configuration.

The compounds of formula (I) contain several asymmetric centres and thus they exist as enantiomers and diastereomers. The invention includes both the separated pure isomers as well as mixtures of isomers. Those compounds are preferred wherein the 2-azaindole carbon atom and the carbon atoms bearing the $R^2$ and $R^3$ substituents have the S-configuration.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts. Salts may also be formed with bases, examples are the alkali metal salts such as the sodium, potassium and calcium salts, or salts with ammonia or amines such as dicyclohexylamine.

The term bioprecursor in the above definition means a pharmaceutically acceptable biologically degradable derivative of the compound of formula (I) which, upon administration to an animal or human being, is converted in the patient's body to produce a compound of the formula (I). Such bioprecursors are well known to those skilled in the art and include, for example, biolabile esters such as the lower alkanoyloxymethyl ester, including alkyl and cycloalkyl-substituted derivatives thereof. Thus a particular example is the 2-methyl-1-propionyloxy-1-propyl ester.

In a preferred group of compounds of formula (I) $R^2$ is 2-phenethyl and $R^3$ is methyl or 4-aminobutyl. $R^1$ is preferably H or ethyl. Particularly preferred are compounds wherein $R^4$ is —$CONR^5R^6$, particularly those wherein $R^5$ is methyl and $R^6$ is H, or wherein $R^4$ is $SO_2R^7$, particularly $SO_2CH_3$.

Particularly preferred individual compounds include 1-[N-(1-S-ethoxycarbonyl-3-phenylpropyl)-S-alanyl]-2-S-carboxy-6-(N-methylcarbamoyl)-octahydro-6-azaindole, 1-[N-(1-S-ethoxycarbonyl-3-phenylpropyl-S- alanyl]-2-S-carboxy-6-methanesulphonyl-octahydro-6-azaindole, and 1-[N-(1-carboxy-3-phenylpropyl)-S-lysyl]-2-carboxy-6-methanesulphonyl-octahydro-6-azaindole.

DETAILED DESCRIPTION OF THE INVENTION

The compounds of formula (I) are prepared by removing the carboxy-protecting group $R^{11}$ from a compound of the formula:

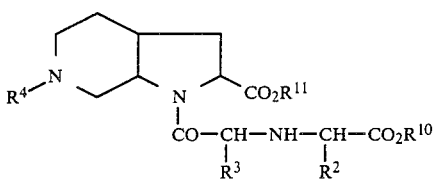

(II)

wherein $R^2$ and $R^3$ are as previously defined, $R^{10}$ is as previously defined for $R^1$ but not including H and $R^{11}$ is a selectively removable carboxylic acid protecting group, and, if desired removing the ester group $R^{10}$, and optionally forming a pharmaceutically acceptable salt of the product.

In this process the carboxylic acid protecting group $R^{11}$ may be any selectively removable ester group which may be removed under mild conditions without degrading the final product of formula (I). In practice a lower alkyl group such as methyl or ethyl is generally satisfactory as this can be readily removed by hydrolysis under mild conditions. In the case when $R^{10}$ is also for example a lower alkyl group this will, of course, also be removed under these conditions to give the compound wherein $R^1$ is H. Other possibilities for $R^{11}$ are the benzyl group or the tertiary-butyl group. These can be removed by catalytic hydrogenation or by treatment with hydrogen chloride under non-aqueous conditions respectively. Under these conditions the group $R^{10}$ is not cleaved.

The starting materials of formula (II) are prepared from a compound of the formula:

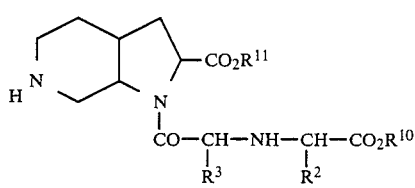

(III)

wherein $R^2$, $R^3$, $R^{10}$ and $R^{11}$ are as previously defined by:

(a) acylation with an acyl halide of the formula:

$R^7COX$ wherein X is a halogen atom preferably bromine or chlorine and $R^7$ is as previously defined to give those compounds of the formula (II) wherein $R^4$ is —$COR^5$ and $R^5$ is other than hydrogen; or formylation with formic acetic anhydride to give those compounds of formula (II) wherein $R^4$ is —COH; or (b) reaction with a haloformate of the formula:

$R^7OCOX$ wherein $R^7$ is as previously defined and X is as defined above, to give those compounds of formula (II) wherein $R^4$ is —$CO_2R^7$; or (c) sulphonylation with a sulphonyl halide or sulphamylation with a sulphamyl halide of the formula:

$R^7SO_2X$ or $R^5R^6NSO_2X$ wherein $R^5$, $R^6$, $R^7$ and X are as previously defined to give those compounds of the formula (II) wherein $R^4$ is —$SO_2R^7$ or —$SO_2NR^5R^6$ respectively; or (d) reaction with an isocyanate of the formula:

$R^7NCO$, $R^7CONCO$ or $R^7SO_2NCO$ wherein $R^7$ is as previously defined to give those compounds of the formula (II) wherein $R^4$ is $CONHR^5$ and $R^5$ is other than hydrogen, $CONHCOR^7$, or $CONHSO_2R^7$ respectively and, if desired acylating or sulphonylating the product wherein $R^4$ is $CONHR^5$ by reaction with a compound of the formula $R^7COX$ or $R^7SO_2X$ wherein X is as previously defined, to yield those compounds of the formula I wherein $R^4$ is —$CON(R^5)COR^7$ or —$CON(R^5)SO_2R^7$ respectively; or alternatively reacting the compound of formula (III) with phosgene followed by a compound of the formula $R^5R^6NH$, wherein $R^5$ and $R^6$ are as previously defined to give those compounds of the formula (II) wherein $R^4$ is $CONR^5R^6$.

Conditions for the various steps (a) to (d) are entirely conventional and the appropriate reagents, as well as suitable solvents and temperatures which may be employed and the periods required for the reaction, will be readily apparent to those skilled in the art by reference to literature precedents and to the preparative Examples provided herewith. The various reagents required are all known compounds, either commercially available or preparable by literature methods. For substituents having reactive centres, e.g. amino or carboxylic acid groups, these will require protection during the reaction and this an be achieved, where required, using the conventional protective techniques of amino-acid chemistry. Such procedures are well known to those skilled in the art and are described in standard text books on the subject such as, for example, Greenstein and Winitz "Chemistry of the Amino Acids", published by John Wiley and Sons, New York, 1961.

The compounds of formula III are prepared from the 6-azaindole (IV) according to the following reaction sequence wherein $R^2$, $R^3$, $R^{10}$ and $R^{11}$ are as previously defined and $P^1$ and $P^2$ are selectively removable nitrogen protecting groups:

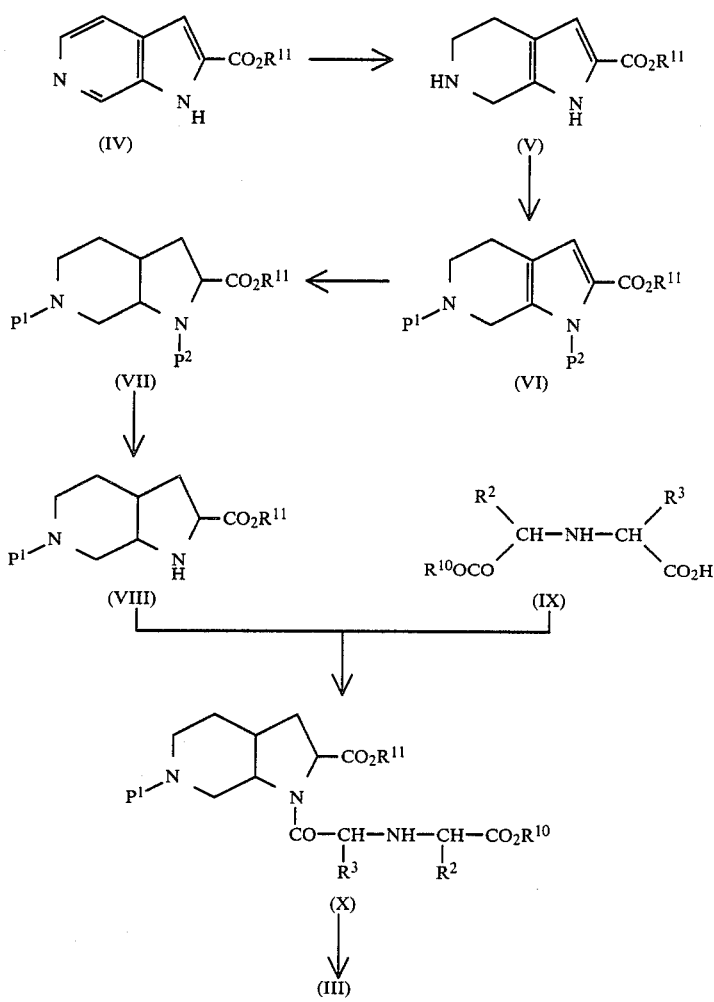

The 6-azaindole (IV) is first reduced by catalytic hydrogenation to give the tetrahydro-6-azaindole (V). This is protected on N-6 and N-1 in turn using conventional selectively removable nitrogen protecting groups. We have found that choice of acetyl or trichloroethoxycarbonyl for N-6 and tertiary-butyloxy carbonyl for N-1 gives satisfactory results. The fully protected compound (VI) is then further reduced by catalytic hydrogenation to yield the octahydro-6-azaindole (VII). This is selectively deprotected to free the N-1 position. In the case where $P^2$ is tertiary-butyloxycarbonyl this is readily achieved by treatment with anhydrous hydrogen chloride at 0° C. The product is then coupled to the N-substituted amino-acid fragment (IX) using a carbodiimide coupling reagent. Removal of the N-6 protecting group is achieved, in the case of trichloroethoxycarbonyl, by treatment with zinc dust and acetic acid, to give the intermediate (III). In a variation of this process the compound of formula (VIII) is coupled to a protected amino acid derivative of formula $P^3NHCH(R^3)CO_2H$ and the protecting group $P^3$ is removed and the product reacted with a compound of formula $CF_3SO_2OCH(R^2)CO_2R^{10}$ to yield the compound of formula (X).

In some instances it is possible to choose for $P^1$ a group required for $R^4$. Thus when acetyl is used, the compound of formula (X) serves directly as the intermediate of formula (II) wherein $R^4$ is —$COCH_3$. Trichloroethoxycarbonyl, methanesulphonyl and N-methylcarbamoyl may be used similarly in the intermediate of formula (X) which may be used directly in the deprotection step to yield the compounds of formula (I) wherein $R^4$ is trichloroethoxycarbonyl, methanesulphonyl or N-methylcarbamoyl respectively. Appropriate reaction conditions for all these steps together with other variants and possibilities will be evident to those skilled in the art.

As previously mentioned, the compounds of the invention are potent inhibitors of angiotensin converting enzyme. Their activity against this enzyme is assessed using a modified procedure based on the assay described by D. W. Cushman and H. S. Cheung, Biochemical Pharmacology, 1971, 20, 1637. The method involves determining the concentration of compound required to reduce by 50% the rate of release of radiolabelled hippuric acid from hippuryl-L-histidyl-L-leucine by angiotensin converting enzyme isolated from rat kidney.

The activity is measured in vivo following intravenous injection to anaesthetised rats as described by I. L. Natoff et al, Journal of Pharmacological Methods, 1981, 5, 305 and by D. M. Gross et al, J. Pharmacol. Exp. Ther., 1981, 216, 552. The dose of inhibitor required to reduce the pressor response produced by intravenous injection of angiotensin I by 50% is determined.

The antihypertensive activity of the compounds is evaluated by measuring the fall in blood pressure following oral or intravenous administration to salt depleted, diuretic primed, spontaneously hypertensive rats or salt depleted renally hypertensive dogs.

For administration to man in the curative or prophylactic treatment of hypertension, oral dosages of the compounds will generally be in the range of from 2–100 mg daily for an average adult patient (70 kg). Thus for a typical adult patient, individual tablets or capsules contain from 1 to 50 mg of active compound, in a suitable pharmaceutically acceptable vehicle or carrier. Dosages for intravenous administration would typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The compounds may be administered alone but may also be administered together with other antihypertensive agents such as diuretics or beta-blockers or such other agents as the physician shall direct to optimise control of blood pressure or to treat congestive heart failure in any particular patient in accordance with established medical practice.

Thus in a further aspect the invention provides a pharmaceutical composition comprising a compound of the formula (I), or a pharmaceutically acceptable salt thereof or bioprecursor therefor, together with a pharmaceutically acceptable diluent or carrier.

The invention also includes a compound of the formula (I), or a pharmaceutically acceptable salt thereof or bioprecursor therefor, for use in medicine, in particular in the treatment of hypertension or congestive heart failure in a human being.

The invention also includes a method of treating hypertension or congestive heart failure which conprises administering an effective amount of a compound of the formula (I) or pharmaceutically acceptable salt thereof or bioprecursor therefor, or pharmaceutical composition as defined above.

The preparation of the compounds of the invention and of intermediates for use in their preparation is illustrated by the following Examples.

EXAMPLE 1

2-Ethoxycarbonyl-1H-pyrrolo[2,3-c]pyridine

This material (hereinafter referred to as 2-ethoxycarbonyl-6-azaindole) was prepared by the literature procedure of M. H. Fisher and A. R. Matzuk, J. Het. Chem., 1969, 6, 775.

EXAMPLE 2

2-Ethoxycarbonyl-4,5,6,7-tetrahydro-6-azaindole and 2-ethoxycarbonyl-6-acetyl-4,5,6,7-tetrahydro-6-azaindole A solution of 2-ethoxycarbonyl-6-azaindole (24.5 g, 0.129 mole) in glacial acetic acid (1 liter) was hydrogenated at 100° C. and 100 psi (6.9 bar) over platinum oxide (3 g) for 24 hours. Further platinum oxide (4 g) was added at this time and hydrogenation continued for a total of 96 hours. The catalyst was removed by filtration and the solvent evaporated under vacuum. The residue was dissolved in water (200 ml) neutralised with 2M sodium hydroxide to pH 11 and the precipitated solid (16.5 g) collected by filtration. The filtrate was extracted with ethyl acetate to provide further product (4 g). The combined solids were dissolved in methanol (50 ml), silica gel (40 g) added and the mixture evaporated to dryness. Chromatography of the adsorbed material on silica gel (300 g) with a chloroform:methanol (20:1) solution removed traces of starting material; further elution with chloroform:methanol (10:1) gave a minor impurity which crystallised upon trituration with diethyl ether as a colourless crystalline solid (3.32 g, 10.9%) m.p. 106°–108° C., which proved to be 2-ethoxycarbonyl-6-acetyl-4,5,6,7-tetrahydro-6-azaindole.

Found: C, 61.00; H, 6.98; N, 11.98. $C_{12}H_{16}N_2O_3$ requires C, 60.99; H, 6.83; N, 11.86%. Finally elution with chloroform:methanol (5:1) followed by evaporation of the eluents gave 2-ethoxycarbonyl-4,5,6,7-tetrahydro-6-azaindole as a colourless crystalline solid (12.9 g, 51.6%), m.p. 169°–169.5° C. Found: C, 61.71; H, 7.34; N, 14.41. $C_{10}H_{14}N_2O_2$ requires C, 61.84; H, 7.26; N, 14.42%.

EXAMPLE 3

2-Ethoxycarbonyl-6-(2,2,2-trichloroethoxycarbonyl)-4,5,6,7-tetrahydro-6-azaindole A solution of 2-ethoxycarbonyl-4,5,6,7-tetrahydro-6-azaindole from Example 2 (8 g, 0.041 mole) in dichloromethane (200 ml) and triethylamine (4.15 g, 0.041 mole) was cooled to 0° C. and treated dropwise over 30 minutes with a solution of 2,2,2-trichloroethyl chloroformate (8.69 g, 0.041 mole) in dichloromethane (50 ml) and stirred subsequently for 30 minutes at room temperature. The mixture was quenched with water (50 ml), the organic layer separated, washed with water (50 ml), dried over sodium sulphate and evaporated to give a yellow oil which was chromatographed on silica gel (150 g) eluting with chloroform and chloroform:methanol (99:1) to give the expected pure product as a colourless solid (13.49 g, 89%), m.p. 126.5°–127° C. (from ether/hexane). Found: C, 42.24; H, 4.09; N, 7.54. $C_{13}H_{15}Cl_3N_2O_4$ requires C, 42,24; H, 4.09; N, 7.58%.

EXAMPLE 4

1-(tert-Butoxycarbonyl)-2-ethoxycarbonyl-6-(2,2,2-trichloroethoxycarbonyl)-4,5,6,7-tetrahydro-6-azaindole A suspension of diethyl ether washed sodium hydride (1.22 g, 0.041 mole) in dry dimethylformamide (50 ml) under nitrogen at 0° C. was treated with a solution of 2-ethoxycarbonyl-6-(2,2,2-trichloroethoxycarbonyl)-4,5,6,7-tetrahydro-6-azaindole from Example 3 (13.4 g, 0.036 mole) in dry dimethylformamide (35 ml) dropwise over 10 minutes. Evolution of hydrogen was noted and the mixture stirred at room temperature for 10 minutes. The solution was cooled to 0° C. and treated dropwise with a solution of di-tert-butylcarbonate (8.94 g, 0.041 mole) in dry dimethylformamide (25 ml) over 10 minutes. The mixture was allowed to stand at room temperature overnight, water (100 ml) added and the resulting solution evaporated under vacuum to low bulk. The residue was diluted with water (200 ml) extracted with ethyl acetate (4×100 ml) the combined extracts washed with water (50 ml) and brine (3×100 ml), dried over sodium sulphate and evaporated to give a brown viscous oil, which was chromatographed on silica gel (250 g) eluting with hexane:dichloromethane (2:1), followed by dichloromethane to give the title product as a pure viscous oil (15.3 g, 80%). Found: C, 46.42; H, 5.08; N, 5.72. $C_{18}H_{23}Cl_3N_2O_6$ requires C, 46.02; H, 4.93; N, 5.96%.

EXAMPLE 5

1-(tert-Butoxycarbonyl)-2-R,S-ethoxycarbonyl-6-(2,2,2-trichloroethoxycarbonyl)-octahydro-6-azaindole A solution of 1-(tert-butoxycarbonyl)-2-ethoxycarbonyl-6-(2,2,2-trichloroethoxycarbonyl)-4,5,6,7-tetrahydro-6-azaindole from Example 4 (15.3 g, 0.033 mole) in ethyl acetate (400 ml) was hydrogenated at 60 psi (4.2 bar) and room temperature over platinum oxide (3 g) overnight. The catalyst was removed by filtration and the filtrate evaporated under vacuum to give a yellow oil which was chromatographed on silica gel (200 g) eluting with dichloromethane:hexane (9:1) and then dichloromethane:methanol (99:1) to give the title product as a pale yellow oil (13.29 g, 87%). Found: C, 46.19; H, 5.86; N, 6.08. $C_{18}H_{27}Cl_3N_2O_6$ requires C, 45.63; H, 5.75; N, 5.91%.

EXAMPLE 6

2-R,S-Ethoxycarbonyl-6-(2,2,2-trichloroethoxycarbonyl)-octahydro-6-azaindole hydrochloride etherate A suspension of 1-(tert-butoxycarbonyl)-2-R,S-ethoxycarbonyl-6-(2,2,2-trichloroethoxycarbonyl)-octahydro-6-azaindole from Example 5 (13.24 g, 0.028 mole) in dry diethyl ether (850 ml) at 0° C. was treated with anhydrous hydrogen chloride gas and stirred at 0° C. for 4 hours. The resultant cloudy solution was evaporated to dryness and the colourless solid obtained was triturated with dry diethyl ether to give the title product as a colourless solid (11.53 g, 95%) with no true m.p. Found: C, 38.80; H, 5.21; N, 6.55. $C_{13}H_{19}Cl_3N_2O_4.HCl.\frac{1}{4}Et_2O$ requires C, 39.22; H, 5.29; N, 6.54%.

EXAMPLE 7

1-(tert-Butoxycarbonyl)-2-ethoxycarbonyl-6-acetyl-4,5,6,7-tetrahydro-6-azaindole A suspension of diethyl ether washed sodium hydride (0.28 g, 0.009 mole) in dry dimethylformamide (8 ml) at 0° C. was treated with a solution of 2-ethoxycarbonyl-6-acetyl-4,5,6,7-tetrahydro-6-azaindole from Example 2 (2 g, 0.0085 mole) in dry dimethylformamide (2 ml) and stirred for 20 minutes. The mixture was warmed to room temperature and stirred for 1 hour by which time solution was complete. The solution was cooled to 0° C., a solution of di-tert-butylcarbonate (1.85 g, 0.0085 mole) in dry dimethylformamide (2 ml) added dropwise over 10 minutes, and the solution stirred at room temperature for 4 hours. The mixture was quenched with water (200 ml), extracted with ethyl acetate (4×100 ml) the organic extracts washed with brine (3×100 ml), dried over sodium sulphate, and evaporated to give a yellow oil which was chromatographed on silica gel (20 g) eluting with dichloromethane:hexane (9:1) to give the title product as a pale yellow oil (1.4 g, 49%). Found: C, 60.12; H, 7.32; N, 8.15. $C_{17}H_{24}N_2O_5$ requires C, 60.70; H, 7.19; N, 8.33%.

EXAMPLE 8

1-(tert-Butoxycarbonyl)-2-R,S-ethoxycarbonyl-6-acetyl-octahydro-6-azaindole

A solution of 1-(tert-butoxycarbonyl)-2-ethoxycarbonyl-6-acetyl-4,5,6,7-tetrahydro-6-azaindole from Example 7 (1.3 g, 0.0039 mole) in ethyl acetate (120 ml) was hydrogenated at 50 psi (3.5 bar) and room temperature over platinum oxide (130 mg) for 18 hours. Further platinum oxide (130 mg) was added and hydrogenation continued for 4 hours at room temperature and 2 hours at 50° C. when reduction was complete. The catalyst was removed by filtration and the filtrate evaporated under vacuum to give a pale yellow oil which was chromatographed on silica gel (12 g) eluting with dichloromethane then with dichloromethane:methanol (98:2) to give the pure title product as a pale yellow oil (1.15 g, 86.5%). Found: C, 59.99; H, 8.24; N, 8.15. $C_{17}H_{28}N_2O_5$ requires C, 59.98; H, 8.29; N, 8.23%.

EXAMPLE 9

2-R,S-Ethoxycarbonyl-6-acetyl-octahydro-6-azaindole hydrochloride hydrate, etherate A solution of 1-(tert-butoxycarbonyl)-2-R,S-ethoxycarbonyl-6-acetyl-octahydro-6-azaindole from Example 8 (1.1 g 0.0032 mole) in a mixture of diethyl ether (100 ml) and ethyl acetate (20 ml) was treated at 0° C. with anhydrous hydrogen chloride gas for a total of 30 minutes. The solvents were removed under vacuum to give a gum which was triturated with diethyl ether and collected by filtration to give the title product as a colourless hygroscopic solid (1.0 g, 100%) solvated with diethyl ether, with no true m.p. Found: C, 49.54; H, 7.89; N, 8.94. $C_{12}H_{20}N_2O_3.HCl.H_2O.\frac{1}{4}Et_2O$ requires C, 49.83; H, 8.20; N, 8.94%.

EXAMPLE 10

N-(1-S-Ethoxycarbonyl-3-phenylpropyl)-S-alanine

This was prepared according to the literature procedure of H. Urbach and R. Henning, Tetrahedron Letters, 1984, 25, 1143.

EXAMPLE 11

1-[N-(1-S-Ethoxycarbonyl-3-phenylpropyl)-S-alanyl]-2-R,S-ethoxycarbonyl-6-acetyl-octahydro-6-azaindole A stirred solution of N-(1-S-ethoxycarbonyl-3-phenylpropyl)-S-alanine from Example 10 (0.97 g, 0.0035 mole), N-methylmorpholine (1.06 g, 0.01 mole)

and N-hydroxybenztriazole (0.47 g, 0.0035 mole) in dry dichloromethane (100 ml) was treated at 0° C. with 1-(3-dimethylaminopropyl)-3-ethylcarbodiimide hydrochloride (0.67 g, 0.0035 mole) and stirred at 0° C. for 30 minutes. 2-R,S-Ethoxycarbonyl-6-acetyl-octahydro-6-azaindole hydrochloride, hydrate, etherate (0.97 g, 0.0035 mole) was added and the solution stirred at room temperature for 18 hours. The reaction mixture was diluted with dichloromethane (100 ml), washed with sodium carbonate solution (10% w/v, 3×50 ml), hydrochloric acid (1M, 3×50 ml), brine (3×50 ml), dried over sodium sulphate and evaporated under vacuum to give an oil which was chromatographed on silica gel (12 g) eluting with dichloromethane:methanol (98.5:1.5) to give the expected title product as a pale yellow oil (0.38 g, 21.7%). Found: C, 64.11; H, 8.09; N, 8.30. $C_{27}H_{39}N_3O_6$ requires C, 64.65; H, 7.84; N, 8.38%.

EXAMPLE 12

1-[N-(1-S-Carboxy-3-phenylpropyl)-S-alanyl]-2-R,S-carboxy-6-acetyl-octahydro-6-azaindole disodium salt, hydrate Sodium hydroxide solution (5M, 1 ml, 0.005 mole) was added to a stirred solution of 1-[N-(1-S-ethoxycarbonyl-3-phenylpropyl)-S-alanyl-2-R,S-ethoxycarbonyl-6-acetyl-octahydro-6-azaindole from Example 11 (0.33 g, 0.00066 mole) in tetrahydrofuran (20 ml) and water (15 ml) and the solution stirred at room temperature overnight. The reaction mixture was evaporated under vacuum and the resulting semi-solid dissolved in water (50 ml) and extracted with diethyl ether (3×20 ml). The aqueous layer was passed through a weakly acidic ion-exchange resin (10 ml resin bed) to remove excess base and the aqueous eluents were evaporated under vacuum to give a semi-solid which was lyophilised from water (5 ml) to give the title product as its fluffy colourless disodium salt (0.17 g, 52.6%). Found: C, 52.50; H, 6.10; N, 7.60. $C_{23}H_{29}N_3O_6Na_2 \cdot H_2O$ requires C, 52.56; H, 6.33; N, 8.00%.

EXAMPLE 13

1-[N-(1-S-Ethoxycarbonyl-3-phenylpropyl)-S-alanyl]-2-R,S-ethoxycarbonyl-6-(2,2,2-trichloroethoxycarbonyl)-octahydro-6-azaindole A stirred solution of N-(1-S-ethoxycarbonyl-3-phenylpropyl)-S-alanine from Example 10 (3.91 g, 0.014 mole) and N-hydroxybenztriazole (1.89 g, 0.014 mole) in dry dichloromethane (90 ml) was treated at 0° C. with 1-(3-dimethylaminopropyl)-3-ethylcarbodiimide hydrochloride (2.95 g, 0.015 mole) and stirred at 0° C. for 5 minutes. 2-R,S-Ethoxycarbonyl-6-(2,2,2-trichloroethoxycarbonyl)-octahydro-6-azaindole hydrochloride etherate from Example 6 (6 g, 0.014 mole) and a solution of N-methylmorpholine (3 g, 0.03 mole) in dry dichloromethane (30 ml) were added, the temperature allowed to rise from 0° C. to room temperature over 3 hours and the reaction mixture was then allowed to stand at room temperature for 72 hours. The solution was washed with water (3×50 ml), sodium carbonate solution (10% w/v, 2×50 ml), dilute hydrochloric acid (1M, 3×50 ml) and water (3×30 ml) and dried over sodium sulphate. The solvent was evaporated under vacuum to give a yellow oil, which was chromatographed on silica gel (150 g) eluting with hexane:ethyl acetate (3:1) to give the pure title material as a pale yellow oil (4.48 g, 50.4%). Found: C, 53.50; H, 6.37; N, 6.36. $C_{28}H_{38}Cl_3N_3O_7$ requires C, 52.96; H, 6.03; N, 6.62%. Separation of the two diastereomers contained in this material was possible by column chromatography on silica gel.

EXAMPLE 14

1-[N-(1-S-Carboxy-3-phenylpropyl)-S-alanyl]-2-R,S-carboxy-6-(2,2,2-trichloroethoxycarbonyl)octahydro-6-azaindole disodium salt A solution of 1-[N-(1-S-ethoxycarbonyl-3-phenylpropyl)-S-alanyl]-2-R,S-ethoxycarbonyl-6-(2,2,2-trichloroethoxycarbonyl)octahydro-6-azaindole from Example 13 (0.23 g, 0.00036 mole) in tetrahydrofuran (20 ml) and water (15 ml) was treated at room temperature with sodium hydroxide solution (5M, 0.6 ml, 0.003 mole) and stirred at room temperature overnight. The solvents were evaporated under vacuum, the resulting semi-solid dissolved in water (50 ml), extracted with diethyl ether (3×20 ml) and the aqueous fraction passed through a weakly acidic ion-exchange resin (15 ml resin bed) to remove excess base. The product rich fractions were combined and lyophilised from water to give the title product as its disodium salt (0.095 g, 42.4%), m.p. 170°–173° C. (decomp). Found: C, 46.96; H, 5.17; N, 6.75. $C_{24}H_{28}Cl_3N_3O_7Na_2$ requires C, 42.28; H, 4.53; N, 6.75%.

EXAMPLE 15

1-[N-(1-S-Ethoxycarbonyl-3-phenylpropyl)-S-alanyl]-2-R,S-ethoxycarbonyl-octahydro-6-azaindole A solution of 1-[N-(1-S-ethoxycarbonyl-3-phenylpropyl)-S-alanyl]-2-R,S-ethoxycarbonyl-6-(2,2,2-trichloroethoxycarbonyl)octahydro-6-azaindole from Example 13 (4.16 g, 0.0066 mole) in glacial acetic acid (100 ml) was treated with freshly activated zinc dust (4 g, 0.06 mole) and stirred at room temperature overnight. The mixture was diluted with water (100 ml), the excess zinc removed by filtration and the solid washed well with chloroform (200 ml). The filtrate was evaporated to dryness, the resulting gum was taken up in water, the solution basified to pH 11 (5M NaOH), diluted with brine (100 ml) and extracted with chloroform (3×100 ml). The organic layer was separated, washed with water (100 ml), dried over sodium sulphate and evaporated to give the pure title product as a viscous foam (2.97 g, 99%).

EXAMPLE 16

1-[N-(1-S-Ethoxycarbonyl-3-phenylpropyl)-S-alanyl]-2-R,S-ethoxycarbonyl-6-benzoyl-octahydro-6-azaindole A solution of 1-[N-(1-S-ethoxycarbonyl-3-phenylpropyl)-S-alanyl]-2-R,S-ethoxycarbonyl-octahydro-6-azaindole from Example 15 (0.498 g, 0.00108 mole) in dry dichloromethane (15 ml) was treated with a solution of N-methylmorpholine (0.109 g, 0.00109 mole) in dichloromethane (5 ml), the solution cooled to 0° C. and treated with benzoyl chloride (0.152 g, 0.00108 mole) in dichloromethane (5 ml) and stirred at room temperature overnight. The solvents were removed under vacuum and the residue partitioned between ethyl acetate (50 ml) and water (20 ml). The organic layer was separated, washed with water (2×20 ml), dried over sodium sulphate and the solvent removed under vacuum to give a yellow oil which was chromatographed on silica gel (7 g) eluting with ethyl acetate:hexane (1:10) and then ethyl acetate:hexane (1:1) to give the title product as a pale yellow oil (0.44 g, 72%).

EXAMPLE 17

1-[N-(1-S-Carboxy-3-phenylpropyl)-S-alanyl]-2-R,S-carboxy-6-benzoyl-octahydro-6-azaindole hydrate A solution of 1-[N-(1-S-ethoxycarbonyl-3-phenylpropyl)-S-alanyl]-2-R,S-ethoxycarbonyl-6-benzoyl-octahydro-6-azaindole from Example 16 (0.42 g, 0.00074 mole) in tetrahydrofuran (10 ml) and water (10 ml) was treated with sodium hydroxide solution (5M, 1.5 ml, 0.0075 mole) and stirred at room temperature overnight. The solvents were removed under vacuum, the semi-solid residue dissolved in water (50 ml), extracted with ethyl acetate (10 ml) and the aqueous layer passed down a strongly acidic ion-exchange resin (15 ml resin bed) and the column eluted with water:pyridine (98:2). The product rich fractions were combined, evaporated and lyophilised from water to give the pure title product as a colourless fluffy solid (0.190 g, 47.3%) m.p. 167°–169° C. (decomp.) Found: C, 62.21; H, 6.35; N, 7.77. $C_{28}H_{33}N_3O_6.2H_2O$ requires C, 61.86; H, 6.85; N, 7.72%.

EXAMPLE 18

1-[N-(1-S-Ethoxycarbonyl-3-phenylpropyl)-S-alanyl]-2-R,S-ethoxycarbonyl-6-hexanoyl-octahydro-6-azaindole This was prepared according to the method of Example 16 by reaction with hexanoyl chloride and was obtained as a pure yellow oil (79%). Found: C, 66.61; H, 8.49; N, 7.18. $C_{31}H_{47}N_3O_6$ requires C, 66.76; H, 8.49; N, 7.53%.

EXAMPLE 19

1-[N-(1-S-Carboxy-3-phenylpropyl)-S-alanyl]-2-R,S-carboxy-6-hexanoyl-octahydro-6-azaindole hydrate This was prepared from the product of Example 18 by hydrolysis following the method of Example 17 and was obtained as a pure colourless solid (28.6%) m.p. 162°–165° C. (decomp.). Found: C, 62.66; H, 7.64; N, 8.13. $C_{27}H_{39}N_3O_6.H_2O$ requires C, 62.40; H, 7.95; N, 8.05%.

EXAMPLE 20

1-[N-(1-S-Ethoxycarbonyl-3-phenylpropyl)-S-alanyl]-2-R,S-ethoxycarbonyl-6-(N-benzyloxycarbonylglycyl)-octahydro-6-azaindole This was prepared from the product of Example 15 by acylation according to the method of Example 16 using the symmetrical anhydride derived from N-benzyloxycarbonyl-glycine and was obtained pure as a viscous oil (76%). Found: C, 64.58; H, 7.23; N, 8.22. $C_{35}H_{46}N_4O_8$ requires C, 64.60; H, 7.12; N, 8.61%.

EXAMPLE 21

1-[N-(1-S-Carboxy-3-phenylpropyl)-S-alanyl]-2-R,S-carboxy-6-(N-benzyloxycarbonylglycyl)-octahydro-6-azaindole hydrate Hydrolysis of the product from Example 20 according to the method of Example 17 gave the title product as a pure colourless crystalline solid (60%) mp 158°–162° C. (decomp.). Found: C, 59.19; H, 6.63; N, 9.28. $C_{31}H_{38}N_4O_8.2H_2O$ requires C, 59.03; H, 6.71; N, 8.88%.

EXAMPLE 22

1-[N-(1-S-Carboxy-3-phenylpropyl)-S-alanyl]-2-R,S-carboxy-6-glycyl-octahydro-6-azaindole hydrate A solution of 1-[N-(1-S-carboxy-3-phenylpropyl)-S-alanyl]-2-R,S-carboxy-6-(N-benzyloxycarbonylglycyl)-octahydro-6-azaindole hydrate from Example 21 (0.24 g, 0.00038 mole) in ethanol (32 ml) and water (8 ml) was hydrogenated at 60 psi (4.1 bar) and room temperature over palladium on charcoal catalyst (5%, 50 mg) for 3 hours. The catalyst was removed by filtration, the filtrate evaporated to low bulk, water removed by chloroform azeotropy and the resulting cream solid triturated with chloroform:hexane (1:1) and collected by filtration to give the title product as a cream coloured solid (0.152 g, 84%) m.p. 172° C. (decomp.). Found: C, 58.06; H, 7.12; N, 10.27. $C_{23}H_{32}N_4O_6.H_2O$ requires C, 57.72; H, 7.73; N, 11.70%.

EXAMPLE 23

1-[N-(1-S-Ethoxycarbonyl-3-phenylpropyl)-S-alanyl]-2-R,S-ethoxycarbonyl-6-(N-methylcarbamoyl)-octahydro-6-azaindole Methyl isocyanate (0.062 g, 0.0012 mole) was added to a stirred solution of 1-[N-(1-S-ethoxycarbonyl-3-phenylpropyl)-S-alanyl]-2-R,S-ethoxycarbonyl-octahydro-6-azaindole from Example 15 (0.5 g, 0.001 mole) in dichloromethane (25 ml) at 0° C. and the solution stirred overnight at room temperature. The solvent was evaporated under vacuum and the oily residue was chromatographed on silica gel (8 g) eluting with dichloromethane then dichloromethane:methanol (98.5:1.5) to give the pure title product as a colourless oil (0.25 g, 49.7%). Found: C, 61.19; H, 7.64; N, 10.31. $C_{27}H_{40}N_4O_6.0.2CH_2Cl_2$ requires C, 61.22; H, 7.63; N, 10.50%.

EXAMPLE 24

1-[N-(1-S-Carboxy-3-phenylpropyl)-S-alanyl]-2-R,S-carboxy-6-(N-methylcarbaoyl)-octahydro-6-azaindole disodium salt, hydrate This was prepared from the product of Example 23 by hydrolysis following the method of Example 14 and the pure title product was obtained as its disodium salt as a fluffy colourless solid (0.159 g, 70%) m.p. 170°–173° C. (decomp.). Found: C, 50.78; H, 6.13; N, 9.82. $C_{23}H_{30}N_4O_6Na_2.5H_2O$ requires C, 50.27; H, 6.42; N, 10.20%.

EXAMPLE 25

1-tert-Butoxycarbonyl-2-R,S-benzyloxycarbonyl-6-(2,2,2-trichloroethoxycarbonyl)-octahydro-6-azaindole A solution of 1-tert-butoxycarbonyl-2-R,S-ethoxycarbonyl-6-(2,2,2-trichloroethoxycarbonyl)-octahydro-6-azaindole (4.2 g, 0.0088 mole) from Example 5 in benzyl alcohol (35 ml) was treated under dry nitrogen with titanium tetraethoxide (0.67 g, 0.0029 mole) and heated to 100° C. for 16 hours. The cooled mixture was acidified with 1M hydrochloric acid and the benzyl alcohol removed by distillation. The residue was dissolved in ethyl acetate (100 ml), washed with brine (50 ml) dried over sodium sulphate and evaporated to give a yellow oil which was chromatographed on silica gel (100 g) eluting with dichloromethane and then dichloromethane/methanol (99:1) to give the pure title product (2.02 g, 43%) as a faintly yellow oil. Found: C, 51.53; H, 5.42; N, 5.09. $C_{23}H_{29}Cl_3N_2O_6$ requires C, 51.55; H, 5.37; N, 5.23%.

EXAMPLE 26

2-R,S-Benzyloxycarbonyl-6-(2,2,2-trichloroethoxycarbonyl)-octahydro-6-azaindole hydrochloride A solution of 1-tert-butoxycarbonyl-2-R,S-benzyloxycarbonyl-6-(2,2,2-trichloroethoxycarbonyl)-octahydro-6-azaindole (1.96 g, 0.00366 mole) from Example 25 in anhydrous diethyl ether (125 ml) at 0° C. was treated with gaseous hydrogen chloride for 30 minutes. The solution was evaporated to dryness and the resultant sticky gum re-dissolved in ether (20 ml) and re-evaporated to give a colourless solid which proved to be the pure title product (1.69 g, 98%). Found: C, 45.44; H, 4.68; N, 6.05. $C_{18}H_{21}Cl_3O_4.HCl$ requires C, 45.78; H, 4.70; N, 5.93%.

EXAMPLE 27

1-[N-(1-S-Ethoxycarbonyl-3-phenylpropyl)-S-alanyl]-2-R,S-benzyloxycarbonyl-6-(2,2,2-trichloroethoxycarbonyl)-octahydro-6-azaindole This was prepared using the general procedure of Example 11 by reaction of the N-hydroxysuccinimide ester of N-(1-S-ethoxycarbonyl-3-phenylpropyl)-S-alanine with 2-R,S-benzyloxycarbonyl-6-(2,2,2-trichloroethoxycarbonyl)-octahydro-6-azaindole from Example 26 and was obtained as a pale yellow oil (60%).

EXAMPLE 28

1-[N-(1-S-Ethoxycarbonyl-3-phenylpropyl)-S-alanyl]-2-R,S-benzyloxycarbonyl-octahydro-6-azaindole A solution of 1-[N-(1-S-ethoxycarbonyl-3-phenylpropyl)-S-alanyl]-2-R,S-benzyloxycarbonyl-6-(2,2,2-trichloroethoxycarbonyl)-octahydro-6-azaindole (1.48 g, 0.00212 mole) from Example 27 in glacial acetic acid (30 ml) was treated with zinc dust (1.5 g) and the mixture stirred at room temperature for 16 hours. The excess metal was removed by filtration and the solid washed with dichloromethane (30 ml) and water (30 ml) and the combined filtrate evaporated to dryness. The oily residue was basified (5M NaOH), extracted with dichloromethane (2×75 ml), the extracts washed with water (50 ml) dried over sodium sulphate and evaporated to give the pure title product as a pale yellow oil (0.97 g, 88%).

EXAMPLE 29

1-[N-(1-S-Ethoxycarbonyl-3-phenylpropyl)-S-alanyl]-2-R,S-benzyloxycarbonyl-6-(N-methylcarbamoyl)-octahydro-6-azaindole A solution of 1-[N-(1-S-ethoxycarbonyl-3-phenylpropyl)-S-alanyl]-2-R,S-benzyloxycarbonyl-octahydro-6-azaindole (0.92 g, 0.00176 mole) from Example 28 in dichloromethane (25 ml) was treated at 0° C. with methyl isocyanate (0.10 g, 0.00175 mole) and stirred for 15 minutes. The solution was evaporated and the resultant yellow oil chromatographed on silica gel (10 g) eluting with ethyl acetate and then ethyl acetate/methanol (98:2) to give the pure title product as a pale yellow oil (0.804 g, 79%). Found: C, 66.40; H, 7.43; N, 10.04. $C_{32}H_{42}N_4O_6$ requires C, 66.04; H, 7.32; N, 9.68%. Separation of the two diastereomers contained in this material was possible by column chromatography on silica gel.

EXAMPLE 30

1-[N-(1-S-Ethoxycarbonyl-3-phenylpropyl)-S-alanyl]-2-R,S-carboxy-6-(N-methylcarbamoyl)-octahydro-6-azaindole hydrate A solution of 1-[N-(1-S-ethoxycarbonyl-3-phenylpropyl)-S-alanyl]-2-R,S-benzyloxycarbonyl-6-(N-methylcarbamoyl)-octahydro-6-azaindole (0.776 g, 0.00134 mole) from Example 29 in ethanol (40 ml) and water (10 ml) was hydrogenated at room temperature and 50 psi (3.5 bar) over palladium on charcoal catalyst (100 mg) for 1 hour. The catalyst was removed by filtration and the filtrate evaporated to low volume and water azeotropically removed by distillation with dichloromethane (3×20 ml) to give the expected pure product as a colourless solid (0.57 g, 83%). No clear m.p. but decomposes slowly over the range 99°–129° C. Found: C, 58.48; H, 7.15; N, 10.58. $C_{25}H_{36}N_4O_6.H_2O.0.1CH_2Cl_2$ requires C, 58.53; N, 7.47; N, 10.88%.

EXAMPLE 31

1-tert-Butoxycarbonyl-2-ethoxycarbonyl-6-azaindole

A stirred suspension of sodium hydride (80%, 0.16 g, 0.0055 mole) in dry N,N-dimethylformamide (5 ml) was treated at 0° C. with a slurry of 2-ethoxycarbonyl-6-azaindole (1.0 g, 0.0053 mole) and stirred at room temperature for 1 hour by which time evolution of hydrogen had ceased and a clear solution was obtained. The mixture was cooled to 0° C., treated with a solution of di-tert-butyl-dicarbonate (1.15 g, 0.0053 mole) and the resulting gel stirred at room temperature for 18 hours. The reaction mixture was poured into ice-water (150 ml) and the solution extracted with ethyl acetate (4×50 ml); the combined organic extracts were washed with brine (3×50 ml) and dried over sodium sulphate. Evaporation of the solvents under vacuum gave an orange oil which was chromatographed on silica gel (12 g) eluting first with hexane and then with a mixture of hexane and ethyl acetate 70:30 to give the pure title product as a pale yellow oil (1.37 g, 90%). Found: C, 62.40; H, 6.35; N, 9.84. $C_{15}H_{18}N_2O_4$ requires C, 62.05; H, 6.25; N, 9.65%.

EXAMPLE 32

1-tert-Butoxycarbonyl-2-R,S-ethoxycarbonyl-octahydro-6-azaindole

A solution of 1-tertbutoxycarbonyl-2-ethoxycarbonyl-6-azaindole (1 g, 0.0037 mole) from Example 31 in ethanol (40 ml) and hydrochloric acid (2M, 2.8 ml) was hydrogenated over platinum oxide at 50 p.s.i. (3.5 bar) and room temperature for 72 hours. The catalyst was removed by filtration and the solvents removed under vacuum to give a semi-solid residue which was dissolved in water (50 ml), basified to pH 7.5 and extracted with ethylacetate (3×50 ml). The organic extracts were dried over sodium sulphate and the solvents removed under vacuum to give the pure title compound as a yellow oil (0.92 g, 90%). Found: C, 59.90; H, 8.91; N, 8.62. $C_{15}H_{26}N_2O_4$ requires C, 60.38; H, 8.78; N, 9.39%.

EXAMPLE 33

1-tert Butoxycarbonyl-2-R,S-ethoxycarbonyl-6-(N-methylcarbamoyl)-octahydro-6-azaindole A solution of methyl isocyanate (0.16 g, 0.0028 mole) in dry dichloromethane (5 ml) was added dropwise to a stirred solution of 1-tert-butoxycarbonyl-2-R,S-ethoxycarbonyl-octahydro-6-azaindole (0.82 g, 0.00275 mole) in dry dichloromethane (10 ml) at 0° C. and the mixture stirred at this temperature for 1 hour. The solvent was evaporated under vacuum and the residue chromatographed on silica gel (12 g) eluting with dichloromethane and a mixture of dichloromethane and methanol 96:4. Evaporation of the relevant fractions gave the pure title compound as a colourless foam (0.88 g, 90%). Found: C, 56.89; H, 7.89; N, 11.78. $C_{17}H_{29}N_3O_5$ requires: C, 57.44; H, 8.22; N, 11.82%.

EXAMPLE 34

1-tert Butoxycarbonyl-2-R,S-carboxy-6-(N-methylcarbamoyl)-octahydro-6-azaindole A solution of 1-tert-butoxycarbonyl-2-R,S-ethoxycarbonyl-6-(N-methylcarbamoyl)-octahydro-6-azaindole (0.4 g, 0.0011 mole) from Example 33 in a mixture of tetrahydrofuran (20 ml), water (10 ml) and methanol (20 ml) was treated with 5M sodium hydroxide solution (1 ml, 0.005 mole) and stirred overnight at room temperature. The solution was evaporated under vacuum and the residue dissolved in water (50 ml) and washed with ethyl acetate (3×20 ml). The aqueous layer was acidified to pH2 with 2M hydrochloric acid and extracted with ethyl acetate. The extracts were dried over sodium sulphate and evaporated to give the pure title product as a colourless foam (0.3 g, 81%): Found: C, 53.78; H, 7.90; N, 11.24. $C_{15}H_{25}N_3O_5.\frac{1}{2}H_2O$. $\frac{1}{3}$ Ethyl acetate requires C, 53.63; H, 7.90; N, 11.49%.

EXAMPLE 35

1-tert-Butoxycarbonyl-2-R,S-benzyloxycarbonyl-6-(N-methylcarbamoyl)-octahydro-6-azaindole A solution of 1-tert-butoxycarbonyl-2-R,S-carboxy-6-(N-methylcarbamoyl)-octahydro-6-azaindole (1 g, 0.003 mole) from Example 34 in a mixture of methanol (20 ml) and water (2 ml) was treated with a solution of cesium carbonate in water to pH 7.5. The mixture was evaporated to dryness, and dehydrated by azeotroping with toluene (3×20 ml) to give a solid, which was suspended in N,N-dimethylformamide (20 ml). Benzyl bromide (0.53 g, 0.003 mole) was added and the mixture stirred at room temperature overnight. The mixture was poured into ice-water (300 ml) and extracted with ethyl acetate (3×100 ml). The combined organic layers were washed with brine (3×100 ml), dried over sodium sulphate and evaporated to give an oil, which was chromatographed on silica gel (10 g) eluting with dichloromethane followed by dichloromethane/methanol 98:2 to give the pure title compound as a colourless foam (0.86 g, 69%). Found: C, 62.93; H, 7.37; N, 9.87. $C_{22}H_{31}N_3O_5$ requires C, 63.29; H, 7.46; N, 10.06%.

EXAMPLE 36

2-R,S-Benzyloxycarbonyl-6-(N-methylcarbamoyl)-octahydro-6-azaindole hydrochloride A solution of 1-tert-butoxycarbonyl-2-R,S-benzyloxycarbonyl-6-(N-methylcarbamoyl)-octahydro-6-azaindole (0.85 g, 0.0020 mole) from Example 35 in dry diethyl ether (80 ml) was treated at 0° C. with gaseous anhydrous hydrogen chloride for 30 minutes. The solvent was evaporated to give a semi-solid, which gave the pure title compound as a colourless solid upon trituration with diethyl ether (0.8 g, 96%). Found: C, 55.41; H, 7.21; N, 10.02. $C_{17}H_{23}N_3O_3HCl.H_2O.\frac{1}{2}Et_2O$ requires: C, 55.80; H, 7.64; N, 10.28%.

EXAMPLE 37

1-[N-(1-S-Ethoxycarbonyl-3-phenylpropyl)-S-alanyl]-2-S-benzyloxycarbonyl-6-(N-methylcarbamoyl)-octahydro-6-azaindole A solution of 2-R,S-benzyloxycarbonyl-6-(N-methylcarbamoyl)-octahydro-6-azaindole hydrochloride (20 g, 0.055 mole) in dry dichloromethane (400 ml) was treated successively at 0° C. with N-methylmorpholine (7.5 g, 0.074 mole), N-hydroxybenztriazole (2.55 g, 0.0188 mole), N-(1-S-ethoxycarbonyl-3-phenylpropyl)-S-alanine (5.26 g, 0.0188 mole) and 1-(3-dimethylaminopropyl)-3-ethylcarbodiimide hydrochloride (3.61 g, 0.0188 mole) and the mixture stirred at room temperature for 1.5 hours. Further quantities of N-methylmorpholine (2.0 g, 0.02 mole), N-hydroxybenztriazole (2.55 g, 0.0188 mole), N-(1-S-ethoxycarbonyl-3-phenylpropyl)-S-alanine (5.26 g, 0.0188 mole) and 1-(3-dimethylaminopropyl)-3-ethylcarbodiimide hydrochloride (3.61 g, 0.018 mole) were added to the re-cooled solution at 0° C. at 2 hours and this was repeated at 4 hours. The solution was then allowed to stand at room temperature for 72 hours. The solvent was removed under vacuum, the residue dissolved in ethylacetate (500 ml), the solution washed successively with 1M hydrochloric acid (3×200 ml), 10% sodium carbonate solution (3×200 ml), and brine (3×200 ml) and dried over sodium sulphate. The solvent was removed under vacuum and the residual oil chromatographed on silica gel (300 g) eluting with ethyl acetate/methanol 97:3 to give the title product as the separated pure diastereomer as a pale yellow oil (9.96 g, 62.6% of theoretical). Found: C, 66.08; H, 7.39; N, 9.48. $C_{32}H_{42}N_4O_6$ requires C, 66.41; H, 7.32; N, 9.68%. $[\alpha]_D^{25} = -54.5°(c=1$, methanol).

EXAMPLE 38

1-[N-(1-S-Ethoxycarbonyl-3-phenylpropyl)-S-alanyl]-2-S-carboxy-6-(N-methylcarbamoyl)-octahydro-6-azaindole A solution of 1-[N-(1-S-ethoxycarbonyl-3-phenylpropyl)-S-alanyl]-2-S-benzyloxycarbonyl-6-(N-methylcarbamoyl)-octahydro-6-azaindole (9.6 g, 0.0166 mole) in ethanol (400 ml) and water (100 ml) was hydrogenated over palladium on charcoal catalyst (1 g) at 50 p.s.i. (3.45 bar) for 2 hours at room temperature. The catalyst was removed by filtration, the filtrate evaporated under vacuum to give a semi-solid which was triturated with diethyl ether, collected by filtration and dried under vacuum to give the pure title compound as a colourless solid (7.8 g, 97%). Found: C, 60.56; H, 7.54; N, 11.05. $C_{25}H_{36}N_4O_6.\frac{1}{2}H_2O$ requires: C, 60.34; N, 7.50; N, 11.26%.

EXAMPLE 39

1-[N-(1-S-Carboxy-3-phenylpropyl)-S-alanyl]-2-S-carboxy-6-(N-methylcarbamoyl)-octahydro-6-azaindole A stirred solution of 1-[N-(1-S-ethoxycarbonyl-3-phenylpropyl)-S-alanyl]-2-S-carboxy-6-(N-methylcarbamoyl)-octahydro-6-azaindole (2.6 g, 0.0055 mole) from Example 38 in tetrahydrofuran (70 ml) and water 40 (ml) was treated with 5M sodium hydroxide solution (6 ml, 0.03 mole) and stirred at room temperature for 72 hours. The solvents were evaporated under vacuum and the resulting semi-solid dissolved in water (50 ml).

The solution was washed with diethyl ether (3×50 ml) and the aqueous layer was passed through a weakly acidic ion-exchange resin (40 ml resin bed) to remove excess base. The aqueous eluents were evaporated under vacuum to give a semi-solid which was triturated with diethyl ether and evaporated to give an off-white powder which was dried to constant weight at 50° C. to give the pure title compound (2.77 g, 93%) m.p. 176°–178° C. (with decomposition). Found: C, 53.82; H, 6.81; N, 10.44. $C_{23}H_{30}N_4O_6Na_2.H_2O.\frac{1}{2}Et_2O$ requires C, 53.66; H, 6.67; N, 10.01%.

EXAMPLE 40

1-[N-(1-S-Ethoxycarbonyl-3-phenylpropyl)-S-alanyl]-2-S-benzyloxycarbonyl-6-(2,2,2-trichloroethoxycarbonyl)-octahydro-6-azaindole A stirred solution of 2-R,S-benzyloxycarbonyl-6-(2,2,2-trichloroethoxycarbonyl)-octahydro-6-azaindole hydrochloride etherate (10.58 g, 0.0224 mole) from Example 26 in dry dichloromethane (200 ml) was treated at 0° C. with N-(1-S-ethoxycarbonyl-3-phenylpropyl)-S-alanine (6.26 g, 0.0224 mole), N-hydroxybenztriazole (3.03 g, 0.0274 mole), N-methylmorpholine (4.53 g, 0.0448 mole) and 1-(3-dimethylaminopropyl)-3-ethyl-carbodiimide hydrochloride (4.29 g, 0.0224 mole) in four equal portions at 2 hourly intervals. The reaction mixture was allowed to warm from 0° C. to room temperature between portionwise additions but was re-cooled to 0° C. at the time of addition of subsequent portions. The reaction mixture was stirred at room temperature for 72 hours. At this time thin layer chromatography revealed some remaining amine starting material and the reaction mixture was cooled to 0° C. and treated with further N-(1-S-ethoxycarbonyl-3-phenylpropyl)-S-alanine (0.49 g, 0.0034 mole), N-hydroxybenztriazole (0.45 g, 0.0034 mole), N-methylmorpholine (0.34 g, 0.0034 mole) and 1-(3-dimethylaminopropyl)-3-ethyl-carbodiimide hydrochloride (0.64 g, 0.0034 mole) and the solution stirred at room temperature for a further 4 hours. The dichloromethane was removed under vacuum and the residue partitioned between ethyl acetate (300 ml) and water (75 ml). The organic layer was washed with water (2×75 ml), 1N hydrochloric acid (4×75 ml), water (2×75 ml), dilute sodium carbonate solution (4×75 ml) and brine (3×50 ml) and dried over sodium sulphate. The solvent was evaporated under vacuum to give a yellow oil, which was chromatographed on silica gel (300 g) eluting with hexane/ethyl acetate 90:10 and then hexane/ethyl acetate 70:30 to give the title material as the pure separated diastereomer as a pale yellow oil (5.9 g, 76% theoretical yield). Found: C, 56.21; H, 5.83; N, 6.03. $C_{33}H_{40}Cl_3N_3O_7$ requires C, 56.86; H, 5.78; N, 6.03%. $[\alpha]_D^{25} = -70°(c=0.12,$ methanol).

EXAMPLE 41

1-[N-(1-S-Ethoxycarbonyl-3-phenylpropyl)-S-alanyl]-2-S-benzyloxycarbonyloctahydro-6-azaindole A solution of 1-[N-(1-S-ethoxycarbonyl-3-phenylpropyl)-S-alanyl]-2-S-benzyloxycarbonyl-6-(2,2,2-trichloroethoxycarbonyl)-octahydro-6-azaindole (5.8 g, 0.00832 mole) in glacial acetic acid (120 ml) was treated with zinc dust (5.8 g, 0.088 mole) and stirred at room temperature overnight. The residual metal was removed by filtration and the solids washed well with water/acetic acid (3:1, 100 ml). The solvents were removed under vacuum, the residue basified to pH10 with 1M sodium hydroxide solution and the solution filtered. The solids were washed well with dichloromethane. The aqueous layer was extracted with dichloromethane (5×100 ml) and the combined organic extracts were washed with brine (2×50 ml), and dried over sodium sulphate. The solvents were removed under vacuum to give the pure title product as a viscous yellow oil (4.34 g, 100%)

EXAMPLE 42

1-[N-(1-S-Ethoxycarbonyl-3-phenylpropyl)-S-alanyl]-2-S-benzyloxycarbonyl-6-methanesulphonyl-octahydro-6-azaindole A solution of 1-[N-(1-S-ethoxycarbonyl-3-phenylpropyl)-S-alanyl]-2-S-benzyloxycarbonyl-octahydro-6-azaindole (1.2 g, 0.0022 mole) from Example 41 in dry dichloromethane (40 ml) was treated at 0° C. with N-methylmorpholine (0.227 g, 0.0022 mole) and then with methanesulphonyl chloride (0.257 g, 0.0022 mole) in dry dichloromethane (5 ml) and the reaction mixture stirred at room temperature for 2 hours. Thin layer chromatography showed a trace of starting amine to be present so further methane sulphonyl chloride (0.026 g, 0.0002 mole) was added and the solution stirred for 30 minutes at 0° C. The solvents were removed under vacuum, the residue dissolved in ethyl acetate (100 ml), the solution washed with water (3×30 ml), dried over sodium sulphate and evaporated under vacuum to give a yellow gum which was chromatographed on silica gel (20 g) eluting with diethyl ether/hexane 90:10 changing to pure diethyl ether, to give the title compound as a colourless gum (1.01 g, 75%). Found: C, 61.84; H, 6.94; N, 6.70. $C_{31}H_{41}N_3O_7S$ requires C, 62.08; H, 6.89; N, 7.01%.

EXAMPLE 43

1-[N-(1-S-Ethoxycarbonyl-3-phenylpropyl)-S-alanyl]-2-S-carboxy-6-methanesulphonyl-octahydro-6-azaindole A solution of 1-[N-(1-S-ethoxycarbonyl-3-phenylpropyl)-S-alanyl]-2-S-benzyloxycarbonyl-6-methanesulphonyl-octahydro-6-azaindole (0.94 g, 0.00157 mole) in a mixture of ethanol (40 ml) and water (10 ml) was hydrogenated by the general procedure of Example 38 and was obtained as a colourless solid (0.722 g, 89%), m.p. 100°–118° C. (decomp.). Found: C, 55.89; H, 7.05; N, 8.02. $C_{24}H_{35}N_3O_7S.\frac{1}{2}H_2O$ requires C, 55.58; H, 7.00; N, 8.10%.

EXAMPLE 44

1-[N-(1-S-Carboxy-3-phenylpropyl)-S-alanyl]-2-S-carboxy-6-methanesulphonyl-octahydro-6-azaindole 1-[N-(1-S-Ethoxycarbonyl-3-phenylpropyl)-S-alanyl]-2-S-carboxy-6-methanesulphonyl-octahydro-b 6-azaindole from Example 43 was hydrolysed following the general method of Example 39 and was obtained as a colourless solid (81%), m.p. 145°–147° C. (decomp). Found: C, 55.53; H, 6.34; N, 8.43. $C_{22}H_{31}N_3O_7S.\frac{1}{2}H_2O$ requires: C, 53.86; H, 6.58; N, 8.56%.

EXAMPLES 45–54

The following compounds were prepared following the general procedures of Examples 42 to 44 starting with 1-[N-(1-S-ethoxycarbonyl-3-phenylpropyl)-S-alanyl]-2-S-benzyloxycarbonyl-octahydro-6-azaindole and reacting with the appropriate acyl or sulphonyl halide followed by hydrogenation and hydrolysis to yield the monoester and diacid products respectively.

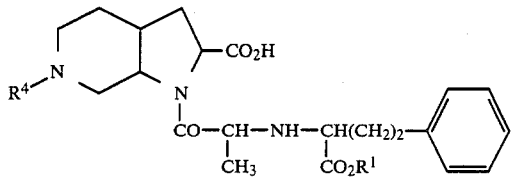

| Example No. | $R^4$ | $R^1$ | m.p. °C. | Analysis % (Theoretical in brackets) | | |
|---|---|---|---|---|---|---|
| | | | | C | H | N |
| 45 | $CH_3NHSO_2$ | $C_2H_5$ | glass[a] | 54.79 (54.38 | 6.99 7.20 | 9.98 10.14) |
| 46 | $CH_3NHSO_2$ | H | [b] | 45.07 (45.12 | 5.73 5.78 | 7.41 9.57) |
| 47 | $(CH_3)_2NCO$ | $C_2H_5$ | foam,[c] | 61.00 (61.04 | 7.70 7.68 | 9.97 10.95) |
| 48 | $(CH_3)_2NCO$ | H | 144–146[d] | 58.14 (58.52 | 6.74 7.36 | 10.96 11.37) |
| 49 | $C_2H_5SO_2$ | $C_2H_5$ | [c] | 56.73 (56.36 | 7.35 7.19 | 7.29 7.89) |
| 50 | $C_2H_5SO_2$ | H | glass | | | |
| 51 | $CH_3CONHCO$ | $C_2H_5$ | glass | | | |
| 52 | $CH_3CONHCO$ | H | glass | | | |
| 53 | $(CH_3)_2NSO_2$ | $C_2H_5$ | 112–128 (dec) | 55.89 (55.74 | 7.32 7.11 | 9.56 10.40) |
| 54 | $(CH_2)_2NSO_2$ | H | 142–146 | 53.23 (53.16 | 6.96 6.97 | 9.82 10.78) |

[a]Hemihydrate, ¼ $Et_2O$
[b]2½ $H_2O$
[c]hemihydrate
[d]hydrate

EXAMPLE 55

1-[N-(1-S-Ethoxycarbonyl-3-cyclohexylpropyl)-S-alanyl]-2-S-carboxy-6-(N-methylcarbamoyl)-octahydro-6-azaindole hydrochloride 1-[N-(1-S-Ethoxycarbonyl-3-phenylpropyl)-S-alanyl]-2-S-carboxy-6-(N-methylcarbamoyl)-octahydro-6-azaindole (0.12 g, 0.00025 mole) in ethanol (30 ml), water (2 ml) and 2M hydrochloric acid (0.12 ml) was hydrogenated over platinum oxide (10 mg) at room temperature and 60 p.s.i. (4.2 bar). The catalyst was removed by filtration, the filtrate evaporated under vacuum and the residue triturated with diethyl ether to give the title product as a colourless solid (100%) m.p. 128°–130° C. (decomp). Found: C, 53.60; H, 8.08; N, 9.45. $C_{25}H_{42}N_4O_6HCl.1\frac{1}{2}H_2O$ 0.1 $Et_2O$ requires: C, 53.80; H, 8.38; N, 9.91%.

EXAMPLE 56

1-[N-(1-S-Carboxy-3-cyclohexylpropyl)-S-alanyl]-2-S-carboxy-6-(N-methylcarbamoyl)-octahydro-6-azaindole This was prepared by hydrolysis of the product of Example 55 following the general procedure of Example 39 and was obtained as an off-white solid (25%). Found: C, 55.52; H, 7.77; N, 10.96. $C_{23}H_{38}N_4O_6.2H_2O$ requires: C, 54.96; H, 8.43; N, 11.15%.

EXAMPLE 57

1-[N-(1-S-Ethoxycarbonyl-3-cyclohexylpropyl)-S-alanyl]-2-S-carboxy-6-methanesulphonyl-octahydro-6-azaindole hydrochloride This was prepared by reduction of the product of Example 43 following the general procedure of Example 55 and was obtained as a colourless solid (100%), m.p. 145°–164° C. (decomp). Found: C, 51.22; H, 7.63; N, 6.36. $C_{24}H_{41}N_3O_7S.HCl.\frac{1}{2}H_2O$ requires C, 51.37; H, 7.72; N, 7.48%.

EXAMPLE 58

1-[N-(1-S-Carboxy-3-cyclohexylpropyl)-S-alanyl]-2-S-carboxy-6-methanesulphonyl-octahydro-6-azaindole This was prepared by hydrolysis of the product of Example 57 following the general procedure of Example 39 and was obtained as a colourless solid (92%), m.p. 150°–155° C. (decomp). Found: C, 53.52; H, 7.77; N, 7.30. $C_{22}H_{37}N_3O_7S.\frac{1}{2}H_2O$ requires C, 53.20; H, 7.71; N, 8.46%.

EXAMPLE 59

1-[N-(1-R,S-Ethoxycarbonyl-3-phenylpropyl)-$N^6$-benzyloxycarbonyl-S-lysyl]-2-R,S-benzyloxycarbonyl-octahydro-6-azaindole A. 2-R,S-Benzyloxycarbonyl-6-(2,2,2-trichloroethoxycarbonyl)octahydro-6-azaindole hydrochloride (5.0 g) was treated with N-t-butyloxycarbonyl-$N^6$-benzyloxycarbonyl-L-lysine (4.02 g), 1-hydroxybenztriazole (1.58 g), N-methylmorpholine (2.46 g) and 1-(3-dimethylaminopropyl)-3-ethyl-carbodiimide hydrochloride (2.64 g) following the general procedure of Example 40 to give 1-(N-t-butyloxycarbonyl-$N^6$-benzyloxycarbonyl-S-lysyl)-2-R,S-benzyloxycarbonyl-octahydro-6-azaindole as a gum (6.04 g, 68.8%).

B. The product from (A) (4.9 g) was dissolved in 98% formic acid (75 ml) and the solution stirred at room temperature for 2½ hours. The solution was concentrated under vacuum and the residual formic acid removed by azeotroping with dichloromethane (2×50 ml). The residual oil was taken up in dichloromethane (200 ml) and the solution washed with aqueous sodium bicarbonate (2×50 ml) and brine (2×50 ml) and dried over magnesium sulphate. Evaporation of the solvent gave the deprotected derivative as a gum (4.15 g). Rf 0.2 (silica, ethylacetate/hexane 2:1).

C. The product from step (B) (4.15 g) was dissolved in dichloromethane (60 ml) at 0° C. and a solution of triethylamine (0.68 g) in dichloromethane (10 ml) added followed by a solution of ethyl 2-trifluoromethanesulphonyloxy-4-phenyl-butyrate (2.3 g) in dichloromethane (10 ml). The solution was allowed to warm to room temperature and was stirred at room temperature for 3 days. The reaction mixture was diluted with dichloromethane (150 ml), washed with 1N hydrochloric acid (3×40 ml), aqueous sodium bicarbonate (3×40 ml), brine (2×40 ml) and dried over magnesium sulphate. The solution was filtered and evaporated to yield a gum which was chromatographed on silica eluting with a mixture of hexane and ethyl acetate. The relevant fractions were combined and evaporated to yield 1-[N-(1-R,S-ethoxycarbonyl-3-phenylpropyl)-$N^6$-benzyloxycarbonyl-S-lysyl]-2-R,S-benzyloxycarbonyl-6-(2,2,2-trichloroethoxycarbonyl)-octahydro-6-azaindole (3.75 g) as a gum.

D. The product from step (C) (4.6 g) was dissolved in glacial acetic acid (150 ml) and treated with zinc dust (4.6 g) following the procedure of Example 41 to yield the title product as a yellowish gum (3.4 g) Rf 0.71 (silica, methyl isobutyl ketone saturated with 50% aqueous acetic acid).

EXAMPLE 60

1-[N-(1-R,S-Ethoxycarbonyl-3-phenylpropyl)-S-leucyl]-2-R,S-benzyloxycarbonyl-octahydro-6-azaindole A. Ethyl 2-bromo-4-phenylbutyrate (9.17 g) in acetonitrile (50 ml) was added to a stirred mixture of L-leucine t-butyl ester (6.14 g, free base) and potassium carbonate (2.4 g) in acetonitrile (60 ml) and the mixture refluxed for 40 hours. The solvent was then evaporated under vacuum and the residue treated with water (50 ml) and extracted with diethyl ether (200 ml). The ether extract was washed with water (3×80 ml), dried over magnesium sulphate, filtered and evaporated to yield an oil. Chromatography on silica, eluting with hexane adding from 1 to 10% diethyl ether gave N-(1-R,S-ethoxycarbonyl-3-phenylpropyl)-S-leucine t-butyl ester as an oil (10.53 g).

B. Dry hydrogen chloride gas was passed into a stirred ice cooled solution of the product (10.53 g) from (A) above in diethyl ether (400 ml) for a period of 12 hours. The solution was evaporated to dryness, traces of HCl being removed by azeotroping with dichloromethane (2×100 ml) and diethyl ether (2×100 ml). The residue was triturated with a mixture of diethyl ether and hexane (200 ml, 1:1) and the resulting solid collected by filtration and dried under vacuum to yield N-(1-R,S-ethoxycarbonyl-3-phenylpropyl)-S-leucine hydrochloride (8.6 g).

C. The product from step (B) (7.58 g) was coupled to 2-R,S-benzyloxycarbonyl-6-(2,2,2-trichloroethoxycarbonyl)octahydro-6-azaindole hydrochloride (10 g) following the general procedure of Example 40 to yield 1-[N-(1-R,S-ethoxycarbonyl-3-phenylpropyl)-S-leucyl]-2-R,S-benzyloxycarbonyl-6-(2,2,2-trichloroethoxycarbonyl)-octahydro-6-azaindole (13.8 g) as a mixture of diastereomers Rf 0.30, 0.36 (silica, ethylacetate/hexane 1:2).

D. The product from step (C) (13.1 g) was dissolved in glacial acetic acid (200 ml) and treated with zinc dust (15.0 g) following the general procedure of Example 41. Chromatography on silica eluting with chloroform adding up to 3% of methanol gave the title product as a mixture of diastereomers (7.24 g) as an oil. Rf 0.62 (silica, chloroform/methanol 8:2).

EXAMPLES 61-64

The following compounds were prepared from the appropriate intermediate of formula III described in Examples 59 and 60 above by reaction with methanesulphonylchloride according to the general procedure of Example 42 followed by catalytic hydrogenation and hydrolysis following the procedures of Examples 38 and 17, to yield the monoester and diacid products respectively.

| Example No. | $R^3$ | $R^1$ | m.p. °C. | Analysis % (Theoretical in Brackets) C | H | N |
|---|---|---|---|---|---|---|
| 61 | $-(CH_2)_4NH_2$ | $C_2H_5$ | — | 55.30 (55.46) | 7.42 7.58 | 9.39 9.58[a] |
| 62 | $-(CH_2)_4NH_2$ | H | Indistinct 144–160° (dec) | 51.98 (52.47) | 6.97 7.06 | 9.10 9.70[b] |
| 63 | $-CH_2CH(CH_3)_2$ | $C_2H_5$ | Indistinct 144–160° (dec) | 56.83 (56.92) | 7.33 7.43 | 7.47 7.38[a] |
| 64 | $-CH_2CH(CH_3)_2$ | H | 120° approx. | 57.11 (57.34) | 7.08 7.12 | 8.28 8.02 |

[a]hydrate;
[b]hydrate, ¼ $CH_2Cl_2$ solvate.

EXAMPLE 65

1-[N-(1-R,S-Ethoxycarbonyl-3-phenylpropyl)-$N^6$-benzyloxycarbonyl-S-lysyl]-2-R,S-benzyloxycarbonyl-6-(N-methylcarbamoyl)-octahydro-6-azaindole This was prepared following the general procedure of Example 59(A)–(C) but using 2-R,S-benzyloxycarbonyl-6-(N-methylcarbamoyl)-octahydro-6-azaindole hydrochloride (Example 36) as starting material in Step (A) rather than the 6-(2,2,2-trichloroethoxycarbonyl) derivative. The product, a mixture of diastereomers, was obtained as a gum (4.3 g). Rf. 0.84 (silica, dichloromethane/methanol/ammonium hydroxide, 90:10:1).

EXAMPLE 66

1-[N-(1,R,S-Ethoxycarbonyl-3-phenylpropyl)-S-leucyl]-2-R,S-benzyloxycarbonyl-6-(N-methylcarbamoyl)-octahydro-6-azaindole This was prepared following the general procedure of Example 60(C) but using 2-R,S-benzyloxycarbonyl-6-(N-methylcarbamoyl)octahydro-6-azaindole hydrochloride (Example 36) as starting material rather than the 6-(2,2,2-trichloroethoxycarbonyl) derivative. The product, a mixture of diastereomers was obtained as a gum (0.35 g). Rf. 0.68, 0.61 (silica, methyl isobutyl ketone saturated with 50% aqueous acetic acid).

EXAMPLE 67–70

The following compounds were prepared from the appropriate intermediates of formula II described in Examples 65 and 66 above by catalytic hydrogenation and hydrolysis following the procedures of Examples 38 and 17 to yield the monoester and diacid products respectively.

[Structural formula showing octahydro-6-azaindole dipeptide with R³, R¹, CO₂R¹, and phenethyl substituents]

| Example No. | R³ | R¹ | m.p. °C. | Analysis % (Theoretical in Brackets) C | H | N |
|---|---|---|---|---|---|---|
| 67 | —(CH₂)₄NH₂ | C₂H₅ | Indistinct 120–140° (dec) | 58.83 (59.22) | 8.13 (7.71) | 12.13 (12.10)$^{(a)}$ |
| 68 | —(CH₂)₄NH₂ | H | Indistinct 120–140° (dec) | 54.47 (56.97) | 7.43 (7.39) | 13.21 (12.62)$^{(b)}$ |
| 69 | —CH₂CH(CH₃)₂ | C₂H₅ | Indistinct 120–140° (dec) | 63.18 (63.35) | 7.97 (7.98) | 10.04 (10.56) |
| 70 | —CH₂CH(CH₃)₂ | H | Indistinct 120–140° (dec) | 59.66 (59.57) | 7.39 (7.34) | 10.75 (10.55)$^{(c)}$ |

$^{(a)}$Solvate with dichloromethane (0.33 mole) and ethanol (0.1 mole).
$^{(b)}$Solvate with dichloromethane (0.33 mole) hemihydrate.
$^{(c)}$Solvate with dichloromethane (0.33 mole).

EXAMPLE 71

1-[N-1-S-Ethoxycarbonyl-3-phenylpropyl)-S-alanyl]-2-S-(2-methyl-1-R,S-propionyloxy-1-propyloxycarbonyl)-6-methanesulphonyloxy-octahydro-6-azaindole hydrochloride, hemihydrate A mixture of 1-[N-(1-S-ethoxycarbonyl-3-phenylpropyl)-S-alanyl]-2-S-carboxy-6-methanesulphonyl-octahydro-6-azaindole (0.5 g), 1-chloro-2-methyl-propyl propionate (0.17 g) and 1,8-diazabicyclo[5.4.0]undec-7-ene was refluxed in acetonitrile (20 ml) for 45 minutes. The solvent was removed under vacuum and the residue chromatographed on Kieselgel silica (19 g) eluting with ethyl acetate. Fractions containing the desired product were combined and evaporated to yield the ester as glass (30 mg) which was converted to its hydrochloride salt using a solution of hydrogen chloride in diethyl ether. Rf. 0.82 (silica, ethyl acetate). Found: C, 54.95; H, 7.61; N, 6.11. $C_{31}H_{47}N_3O_9S.HCl.0.5H_2O$ requires C, 54.49; H, 7.23; N, 6.15%.

What is claimed is:

1. An octahydro-6-azaindole dipeptide derivative of the formula:

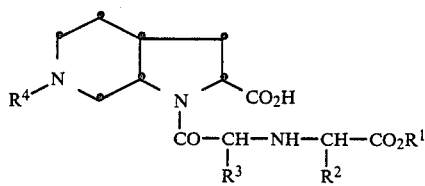

or a pharmaceutically acceptable salt thereof, wherein:
$R^1$ is hydrogen, $C_1$-$C_6$ alkyl, $C_2$-$C_6$ alkenyl or aryl-($C_1$-$C_4$ alkyl);
$R^2$ is $C_1$-$C_6$ alkyl, $C_2$-$C_6$ alkenyl, $C_3$-$C_7$ cycloalkyl or substituted $C_1$-$C_6$ alkyl in which the substituent is halogen, hydroxy, $C_1$-$C_6$ alkoxy, aryl, aryloxy, aryl-($C_1$-$C_4$ alkoxy), $C_1$-$C_4$ alkylthio, arylthio, aryl-($C_1$-$C_4$ alkyl)thio, $C_3$-$C_7$ cycloalkyl, —NR⁵R⁶, —NHCOR⁵, —NHCOOR⁷, guanidino or a heterocyclyl group;
$R^3$ is $C_1$-$C_6$ alkyl, $C_3$-$C_7$ cycloalkyl or substituted $C_1$-$C_6$ alkyl in which the substituent is halogen, hydroxy, $C_1$-$C_4$ alkoxy, $C_1$-$C_4$ alkylthio, $C_3$-$C_7$ cycloalkyl, —NR⁵R⁶, —NHCOR⁵, —NHCOOR⁷, —COOH, —COO($C_1$-$C_4$ alkyl), —CONR⁵R⁶, guanidino, aryl or a heterocyclyl group; and
$R^4$ is —SO₂R⁷ or —SO₂NR⁵R⁶, wherein
$R^5$ and $R^6$ are each independently hydrogen, $C_1$-$C_6$ alkyl, $C_3$-$C_7$ cycloalkyl, aryl, heterocyclyl or a substituted $C_1$-$C_6$ alkyl group in which the alkyl group is substituted by one or more halogen atoms or an hydroxy or a $C_3$-$C_7$ cycloalkyl, aryl, heterocyclyl or —NR⁸R⁹ group wherein R⁸ and R⁹ are each independently hydrogen, $C_1$-$C_4$ alkyl, —CO($C_1$-$C_4$ alkyl) or aryl; and
$R^7$ is $C_1$-$C_6$ alkyl, $C_3$-$C_7$ cycloalkyl, aryl, heterocyclyl or a substituted $C_1$-$C_6$ alkyl group in which the alkyl group is substituted by one or more halogen atoms or an hydroxy or a $C_3$-$C_7$ cycloalkyl, aryl, heterocyclyl or —NR⁸R⁹ group;
said aryl groups in the definition of $R^1$, $R^2$, $R^3$ and $R^4$ having up to ten carbon atoms in the nuclear ring; and
said heterocyclyl groups in the definition of $R^2$, $R^3$ and $R^4$ being pyridyl, furyl, thienyl, benzothienyl, indolyl, imidazolyl, thiazolyl, pyrrolidinyl, piperidino, morpholino or piperazinyl, with said groups being optionally substituted with halogen, hydroxy, oxo, $C_1$-$C_4$ alkyl, carbamoyl, amino or mono- or di-($C_1$-$C_4$ alkyl)amino groups.

2. A compound as claimed in claim 1 wherein each aryl group is naphthyl or phenyl optionally substituted with halogen, hydroxy, trifluoromethyl, $C_1$-$C_4$ alkyl, $C_1$-$C_4$ alkoxy, cyano, amino or mono- or di-($C_1$-$C_4$ alkyl)amino groups.

3. A compound as claimed in claim 1 wherein $R^1$ is hydrogen or $C_1$-$C_6$ alkyl.

4. A compound as claimed in claim 3 wherein $R^1$ is hydrogen.

5. A compound as claimed in claim 3 wherein $R^1$ is ethyl.

6. A compound as claimed in claim 1 wherein $R^2$ is substituted $C_1$-$C_6$ alkyl in which the substituent is aryl.

7. A compound as claimed in claim 6 wherein $R^2$ is 2-phenethyl.

8. A compound as claimed in claim 1 wherein $R^3$ is $C_1$-$C_6$ alkyl.

9. A compound as claimed in claim 8 wherein $R^3$ is methyl.

10. A compound as claimed in claim 1 wherein $R^3$ is substituted $C_1$-$C_6$ alkyl in which the substituent is —NR⁵R⁶ wherein R⁵ and R⁶ are each hydrogen.

11. A compound as claimed in claim 10 wherein $R^3$ is 4-aminobutyl.

12. A compound as claimed in claim 1 wherein $R^4$ is —SO₂R⁷.

13. A compound as claimed in claim 12 wherein $R^4$ is —SO₂R⁷ wherein R⁷ is $C_1$-$C_6$ alkyl.

14. A compound as claimed in claim 13 wherein $R^4$ is —SO₂CH₃.

15. A compound as claimed in claim 1 wherein $R^1$ is hydrogen or ethyl, $R^2$ is 2-phenethyl, $R^3$ is methyl or 4-aminobutyl and $R^4$ is —SO₂CH₃.

16. A compound as claimed in claim 1 wherein the 2-azaindole carbon atom and the carbon atoms bearing the $R^2$ and $R^3$ substituents have the S-configuration.

17. 1-[N-(1-S-Ethoxycarbonyl-3-phenylpropyl)-S-alanyl]-2-S-carboxy-6-methanesulphonyl-octahydro-6-azaindole.

18. 1-[N-(1-Carboxy-3-phenylpropyl)-S-lysyl]-2-carboxy-6-methanesulphonyl-octahydro-6-azaindole.

19. A pharmaceutical composition suitable for oral or parenteral administration comprising a pharmaceutically acceptable carrier and an effective antihypertensive amount of a compound of a compound as claimed in claim 1.

20. A method for lowering blood pressure in the treatment of a hypertensive subject, which comprises administering to said subject an effective blood pressure lowering amount of a compound as claimed in claim 1.

* * * * *